(12) United States Patent
Winkler

(10) Patent No.: US 8,597,354 B2
(45) Date of Patent: Dec. 3, 2013

(54) VERTEBRAL IMPLANT

(75) Inventor: Tobias Winkler, Binswangen (DE)

(73) Assignee: Ulrich GmbH & Co.KG, Ulm (DE)

( * ) Notice: Subject to any disclaimer, the term of this patent is extended or adjusted under 35 U.S.C. 154(b) by 66 days.

(21) Appl. No.: 13/293,261

(22) Filed: Nov. 10, 2011

(65) Prior Publication Data

US 2012/0239147 A1 Sep. 20, 2012

(30) Foreign Application Priority Data

Mar. 14, 2011 (DE) .......................... 10 2011 001 251

(51) Int. Cl.
 *A61F 2/44* (2006.01)
(52) U.S. Cl.
 USPC ....................................... 623/17.11
(58) Field of Classification Search
 USPC ............................ 623/17.11–17.16
 See application file for complete search history.

(56) References Cited

U.S. PATENT DOCUMENTS

| | | | | |
|---|---|---|---|---|
| D19,102 S | * | 5/1889 | Staynee | D11/79 |
| D40,888 S | * | 9/1910 | Fishel | D11/90 |
| 2,616,199 A | * | 11/1952 | Robins | 428/9 |
| 3,411,228 A | * | 11/1968 | Lacey | 40/124.01 |
| 3,913,295 A | * | 10/1975 | Thompson | 52/659 |
| D246,636 S | * | 12/1977 | Cone | D11/89 |
| 4,094,091 A | * | 6/1978 | Kupperman et al. | 446/176 |
| 6,663,632 B1 | | 12/2003 | Frigg | |
| D500,964 S | * | 1/2005 | Lach | D11/131 |
| 7,087,082 B2 | * | 8/2006 | Paul et al. | 623/17.11 |
| D533,105 S | * | 12/2006 | Lach | D11/131 |
| 7,887,569 B2 | | 2/2011 | Frigg | |
| 2006/0083869 A1 | * | 4/2006 | Laudick | 428/7 |
| 2010/0324686 A1 | | 12/2010 | Gerner | |

FOREIGN PATENT DOCUMENTS

WO 2010145627 A 12/2010

* cited by examiner

*Primary Examiner* — Mary Hoffman
(74) *Attorney, Agent, or Firm* — Andrew Wilford

(57) ABSTRACT

A vertebral implant has a body extending along a body axis, having a pair of ends, and adapted to be fitted with its ends axially juxtaposed with respective confronting vertebral faces. An inner ring can pivot on one of the ends of the body about a first axis extending transversely of the body axis through the body, and an outer ring can pivot on the inner ring about a second axis extending nonparallel to the first axis transversely of the body axis through the inner ring and body. The outer ring has an end face adapted to engage the respective vertebral face.

21 Claims, 3 Drawing Sheets

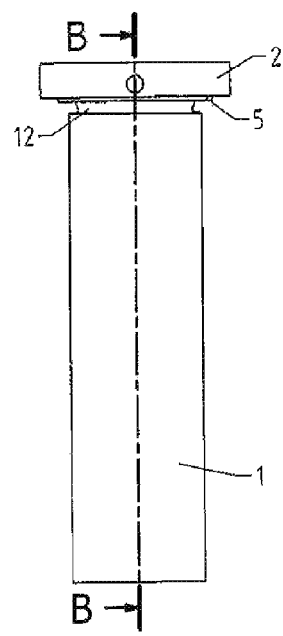
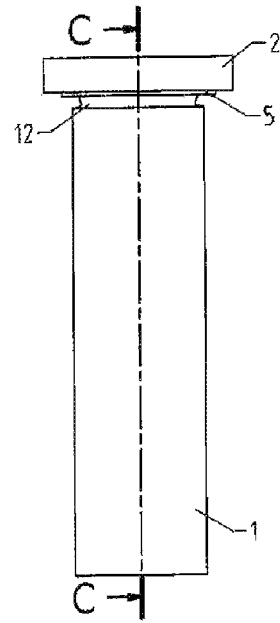
Fig. 4
Fig. 5
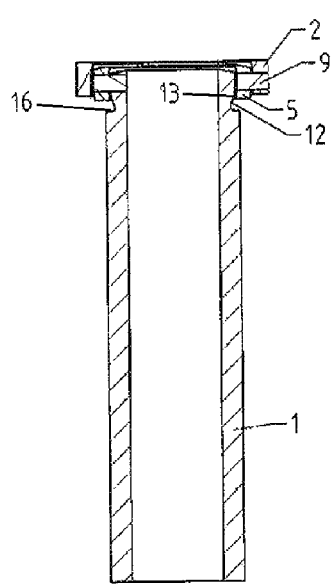
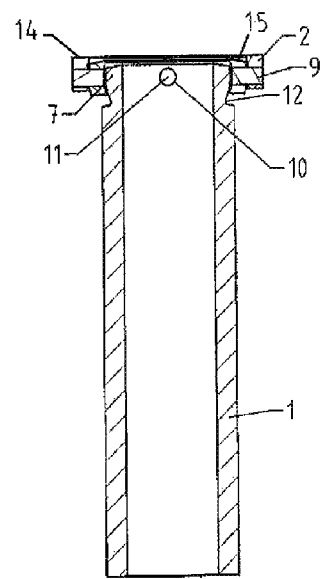
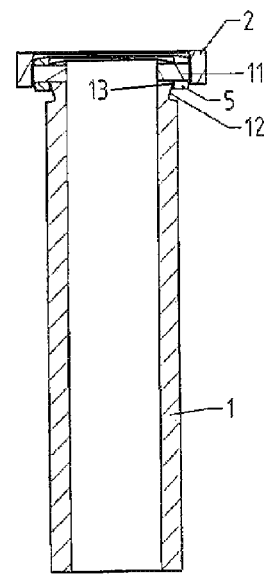
Fig. 6
Fig. 7
Fig. 8

VERTEBRAL IMPLANT

FIELD OF THE INVENTION

The present invention relates to an orthopedic implant. More particularly this invention concerns an implant for replacing one or more spinal vertebrae.

BACKGROUND OF THE INVENTION

One or more spinal vertebrae lost to trauma or degenerative disease can be replaced by an implant typically made of metal and serving to be fitted between the healthy vertebrae flanking the lost vertebra or vertebrae so that the critical spinal chord is not crushed or otherwise injured. Since a typical vertebra is flanked by elastically deformable cartilage disks that allow the spine to flex, it is desirable for the implant to also allow such movement. Thus the implant must be very strong in an axial or longitudinal direction parallel to the spinal column, while at the same time being capable of some sort of flexing so that at least one of its ends can move about an axis perpendicular to the axis of the appliance Accordingly WO 2010/145,627 of Gerner proposes an implant having a basically cylindrical body extending along a main axis and a pair of end rings that can tip somewhat so that their outwardly directed end faces, which typically bear against and/or are anchored to the flanking healthy vertebrae, can tip and assume positions forming large acute angles to this axis. The rings are rotation symmetrical to the main axis and are each formed with a radially inwardly open annular groove that fits over a radially outwardly projecting annular ridge of the body of the implant. Such an implant allows for different angular positions or orientations of the end plate or ring, but it has the disadvantage that it might cant when the plate tilts with to the implant body. The canting can be released again only by applying strong pressure on the opposite side of the plate.

OBJECTS OF THE INVENTION

It is therefore an object of the present invention to provide an improved vertebral implant.

Another object is the provision of such an improved vertebral implant that overcomes the above-given disadvantages, in particular that an angularly variable and easier movement of the plate is ensured.

SUMMARY OF THE INVENTION

A vertebral implant has according to the invention a body extending along a body axis, having a pair of ends, and adapted to be fitted with its ends axially juxtaposed with respective confronting vertebral faces. An inner ring can pivot on one of the ends of the body about a first axis extending transversely of the body axis through the body, and an outer ring can pivot on the inner ring about a second axis extending nonparallel to the first axis transversely of the body axis through the inner ring and body. The outer ring has an end face adapted to engage the respective vertebral face.

This embodiment has the advantage that a continuously variable and unlimited mobility and therefore the best adaptation to the end plate geometry and the end plate angle is provided. Due to the continuously variable adaptation to the end plate angle, peak loads and the fracturing of the vertebra associated therewith can be prevented. This polyaxial joint maintains at least partially the mobility of the spine. In addition, there is higher precision during installation. Compared to conventional implants functioning as vertebral body replacement, the implant of the invention has fewer parts. A plurality of angular positions can be covered with one single implant, so a simple selection of the correct implant, a simple handling of the implant and a reduced stock-keeping are ensured.

It was found to be advantageous if the first axis and/or the second axis are oriented in each case perpendicular to the longitudinal implant axis, so it is easy to manufacture the implant. It is possible here that the first axis and the second axis are spaced apart at different distances from the implant's end facing the end plate, thus are arranged axially offset.

It is further advantageous if the first axis and the second axis are oriented such that they are coplanar in a rest position. Thereby, the first axis and the second axis intersect, which results in a safe application.

A more secure locking of the ring and the inner ring is provided by the advantageous formation of an annular collar on the body.

It is particularly favorable if the inner ring has at least one pin seat for receiving at least one pin of the body and formed along the first axis. A pin journal in the inner ring allows a simplified assembly of the implant and ensures secure mounting. It was found to be useful if the pin seat and the pin of the inner ring are provided in duplicate for a stable and secure mounting of the inner ring on the body is created.

A further advantage is if the outer ring has at least one pin seat for receiving at least one pin fixed in the inner ring and centered on the second axis. Here too, the mounting of the outer ring on the body by means of a pin makes sense because pivoting about the second axis is made easier. Furthermore according to the invention the implant pin seat of the outer ring and the implant pin of the inner ring and extending along the second axis twice so that a secure and stable mounting of the outer ring on the inner ring is ensured.

Another advantageous embodiment is characterized in that the inner ring and/or the outer ring have/has at least one axially formed recess on the side facing away from the vertebral body, whereby the inner ring or the outer ring, when tilting about the first or the second axis, abuts only later against the body and thereby, an even larger pivoting angle is created.

Furthermore, it is advantageous if the inner ring and/or the outer ring have/has at least one radially formed recess on the side facing the body, whereby also the deflection angle of the inner ring or the outer ring is increased.

It was found to be particularly useful that the body has an annular groove on the outer surface. The annular groove serves as limit stop for the movement of the ring or the end ring, whereby the angle for pivoting the same is increased.

Another advantage involves the fact that the inner ring and/or the outer ring have/has a concave surface on the side facing the body, whereby the inner ring and/or the outer ring are/is guided more carefully on the body or the inner ring. This sliding guide is improved in that according to an advantageous embodiment, the inner ring has a convex surface on the side facing radially of the body axis away from the body.

BRIEF DESCRIPTION OF THE DRAWING

The above and other objects, features, and advantages will become more readily apparent from the following description, reference being made to the accompanying drawing in which:

FIG. 4 is a side elevational view of the implant;

FIG. 5 is a view like FIG. but 4 rotated by 90° about the longitudinal implant axis;

FIG. 6 is a section taken along line A-A of FIG. 3;

FIG. 7 is a section taken along line B-B of FIG. 4; and

FIG. 8 is a section taken along line C-C of FIG. 5.

DETAILED DESCRIPTION

Figure 1:
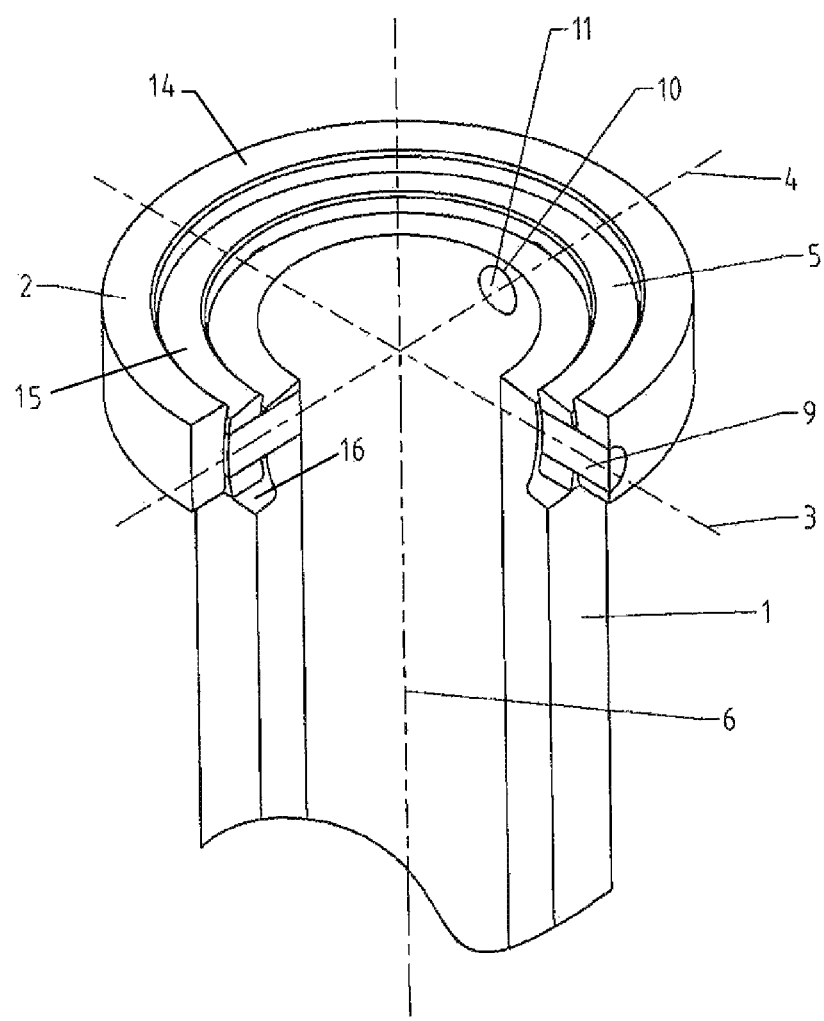
FIG. 1 is a partly perspective view of the invention.
Figure 2A:
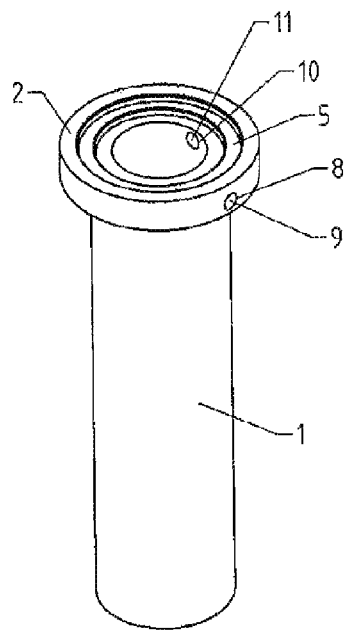
FIG. 2a-2c are perspective views of the implant in different positions.
Figure 2B:
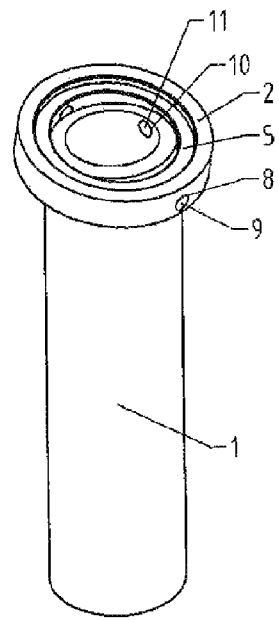
Figure 2C:
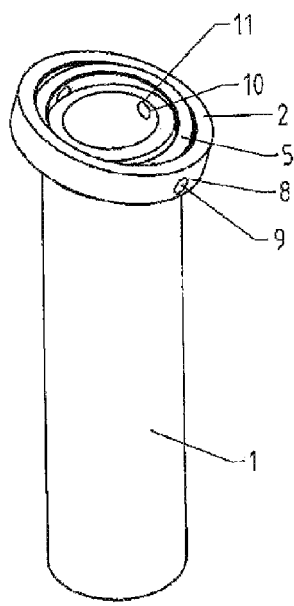
Figure 3:
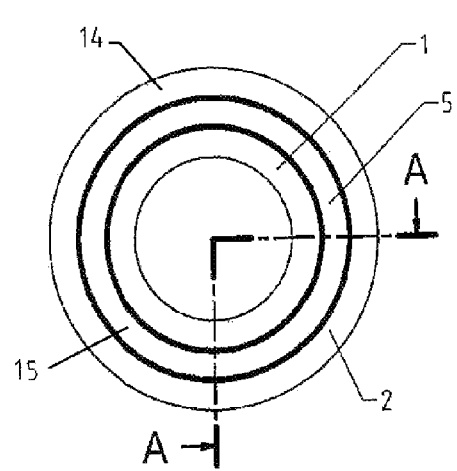
FIG. 3 is a top view of the invention.

As seen in FIG. 1, an implant according to the invention has a body 1 that here is of cylindrically tubular shape and centered on a normally vertical axis 6, and an outer end ring 2 that can pivot on the body 1 about first and second axes 3 and 4 that are perpendicular to each other and coplanar. In the rest position of FIGS. 1, 2a, and 4-8 the plane of the axes 3 and 4 is perpendicular to the axis 6 so that a planar end face 14 of the ring 2 also lies in a plane perpendicular to the axis 6, but as shown in FIGS. 2a-2c, both of these planes can tip or swivel to form relative to the axis 6 a large acute angle or, conversely, a small acute axis relative to a plane perpendicular to the axis 6. In use as is known the ring 2 bears against an unillustrated vertebral face at one axial end of the implant, and another such ring 6 may be provided at the opposite end bearing against a confronting face of another vertebra, and the end face 14 of each such ring 2 can be formed with barbs or teeth to anchor it in the respective vertebra.

More particularly with this joint, the mobility of the spine is maintained so that, on the one hand, an optimal adaptation to the end plate angle of the vertebral body and therefore an optimal contact with reduced surface pressure is achieved to reduce the risk of a point load fracturing the vertebral body. On the other hand, postoperative adaptation is also possible to prevent load peaks caused by micro-movements when in use. Accordingly, with a preferred embodiment of the present invention it is also possible to go without a replacement of a vertebral body and to replace only the intervertebral disk located between two vertebral bodies.

In the illustrated embodiment, the outer end ring 2 has at one outer end 7 two diametrically opposite cylindrical bores or seats 8 rotatably receiving respective pivot pins 9 extending radially outwardly from an inner ring 5 and centered on the first axis 3. In addition, this inner ring 5, which in the FIG. 1 rest position is concentric to the outer ring 2, has two diametrally opposite bores or pin seats 10 in which rotationally engage respective pins 11 fixed in the body 1 and centered on the second axis 4.

The outer surface of the body 1 level with the inner and outer rings 2 and 5 has an annular portion 12 of outwardly convex shape with a center of curvature at a point where the axes 3 and 4 meet the axis 6. An annular shoulder surface 16 lying in a plane perpendicular to the axis 6 serves as a stop limiting pivoting of the ring 5 about the axis 11. The inner ring has a complementary inner surface 13 of shorter axial length that rides in surface contact on the portion 12. Thus as the outer rings 2 and 5 tip about the axes 3 and 4, the inner ring 5 remains in solid surface contact with the body 1. An outer face 15 of the inner ring 5 lying inside the outer face 14 of the outer ring 2 is axially recessed inward toward the body 1 of this face 14 and is frustoconically outwardly tapered so that during maximum swiveling of the two rings 2 relative to each other this end face 15 will lie inward of a plane of the face 14 and not engage the vertebra against which the face 14 normally bears directly.

FIGS. 1 and 2a shows the implant in a perspective and partial sectional view, the pin 9 and the implant pin 11 which allow the polyaxial alignment of the outer end ring 2 for adapting to the end plate of the vertebral body are clearly visible. Here the axes 3 and 4 are perpendicular to the axis 6.

In FIG. 2b, the implant is illustrated with both rings 5 rotated about the second axis 4.

FIG. 2c shows the inner ring 5 pivoted about the axis 4 relative to the body 1 and the outer ring 2 pivoted about the axis 3 relative to the inner ring 5 so that this outer ring 2 is totally skew (neither parallel nor perpendicular) to a plane including the axes 3 and 4.

I claim:

1. An implant for installation between two adjacent spinal vertebrae, the implant comprising:

a body extending along a body axis, fittable between the adjacent vertebrae, having a pair of ends, and adapted to be fitted with its ends axially juxtaposed with respective confronting faces of the two adjacent vertebrae, the body having at one of the ends a radially outwardly directed convex outer surface;

an inner ring pivotal on the one end of the body about a first axis extending transversely of the body axis through the body, the inner ring having a radially inwardly directed concave inner surface riding on the outwardly convex surface of the one end of the body; and an outer ring pivotal on the inner ring about a second axis extending nonparallel to the first axis transversely of the body axis through the inner ring and body, the outer ring having an end face adapted to engage the respective vertebral face, the outer ring being pivotal on the inner ring and the inner ring being pivotal on the body for force-transmission between the outer ring and the body through the inner body.

2. The vertebral implant defined in claim 1 wherein, in a rest position with the outer-ring end face perpendicular to the body axis, at least one of the first and second axes is perpendicular to the body axis.

3. The vertebral implant defined in claim 2 wherein, in the rest position, both the first axis and the second axis are perpendicular to the body axis and perpendicular to each other.

4. The vertebral implant defined in claim 1 wherein the first and second axes are coplanar.

5. The vertebral implant defined in claim 1 further comprising:

an inner pivot pin extending along the first axis and seated in the body and the inner ring.

6. The vertebral implant defined in claim 5 wherein the inner pin is fixed in the body and pivotal in a seat in the inner ring.

7. The vertebral implant defined in claim 5 wherein there are two of the inner pins projecting diametrally oppositely from the body on opposite sides of the body axis and each seated in the inner ring.

8. The vertebral implant defined in claim 1 further comprising:

an outer pivot pin extending along the second axis and seated in the inner ring and the outer ring.

9. The vertebral implant defined in claim 8 wherein the outer pin is fixed in the inner ring and pivotal in a seat in the outer ring.

10. The vertebral implant defined in claim 8 wherein there are two of the outer pins projecting diametrally oppositely from the inner ring on opposite sides of the body axis and each seated in the outer ring.

11. The vertebral implant defined in claim 1 wherein the inner surface and the outer surface of the body radially confronting and riding on the inner-ring inner surface are annular and complementarily arcuate.

12. The vertebral implant defined in claim 11 wherein the inner and outer surfaces have centers of curvature lying at an intersection of the first and second axes.

13. The vertebral implant defined in claim 12 wherein the intersection lies on the body axis.

14. An implant for installation between two adjacent spinal vertebrae, the implant comprising:
- a rigid tubular body extending along a body axis, fittable between the adjacent vertebrae, having a pair of ends, and adapted to be fitted with its ends axially juxtaposed with respective confronting faces of the two adjacent vertebrae, the body having at one end a radially outwardly directed convex outer surface;
- an inner ring pivotal on the one end of the body about a first axis extending transversely of the body axis through the body, the inner ring having a radially inwardly directed concave inner surface riding on the outwardly convex surface of the one end of the body; and
- an outer ring pivotal on the inner ring about a second axis extending nonparallel to the first axis transversely of the body axis through the inner ring and body, the outer ring having an end face adapted to engage the respective vertebral face.

15. The vertebral implant defined in claim 14 wherein, in a rest position with the outer-ring end face perpendicular to the body axis, at least one of the first and second axes is perpendicular to the body axis.

16. The vertebral implant defined in claim 15 wherein, in the rest position, both the first axis and the second axis are perpendicular to the body axis and perpendicular to each other.

17. The vertebral implant defined in claim 14 wherein the first and second axes are coplanar.

18. The vertebral implant defined in claim 14 further comprising:
- an inner pivot pin extending along the first axis, seated in the body and the inner ring, fixed in the body, and pivotal in a seat in the inner ring.

19. The vertebral implant defined in claim 18 wherein there are two of the inner pins projecting diametrically oppositely from the body on opposite sides of the body axis and each seated in the inner ring.

20. The vertebral implant defined in claim 14 further comprising:
- an outer pivot pin extending along the second axis, seated in the inner ring and the outer ring, fixed in the inner ring, and pivotal in a seat in the outer ring.

21. An implant for installation between two adjacent spinal vertebrae, the implant comprising:
- a body extending along a body axis, fittable between the adjacent vertebrae, having a pair of ends, and adapted to be fitted with its ends axially juxtaposed with respective confronting faces of the two adjacent vertebrae;
- an inner ring pivotal on one of the ends of the body about a first axis extending transversely of the body axis through the body; and
- an outer ring pivotal on the inner ring about a second axis extending nonparallel to the first axis transversely of the body axis through the inner ring and body, the outer ring having an end face adapted to engage the respective vertebral face, the outer ring being pivotal on the inner ring and the inner ring being pivotal on the body for force-transmission between the outer ring and the body through the inner body, the first axis and the second axis being spaced at different distances from the outer-ring end face and being offset axially of the body axis.

* * * * *